United States Patent [19]
Kulig et al.

[11] 3,969,820
[45] July 20, 1976

[54] COMPOSITE DOWEL PIN FOR DENTAL MODELS

[75] Inventors: Frank M. Kulig, Bloomfield; Robert A. Semrow, Southington; Harry P. Yorgensen, Jr., Manchester, all of Conn.

[73] Assignee: The J. M. Ney Company, Bloomfield, Conn.

[22] Filed: Feb. 21, 1975

[21] Appl. No.: 551,628

[52] U.S. Cl. ................................................. 32/11
[51] Int. Cl.² ........................................... A61C 13/00
[58] Field of Search ............................. 32/11, 40 R

[56] References Cited
UNITED STATES PATENTS 3,153,283  10/1964  Weissman ......................... 32/40 R
3,518,761  7/1970  Susman et al. ........................ 32/11

Primary Examiner—Robert Peshock

[57] ABSTRACT

A composite dowel pin on which a tooth form may be cast for use in a dental model comprises a body member of synthetic resin tapering to a reduced cross section at one end and a generally cylindrical metal pin extending longitudinally through and outwardly of at least the other end of the body member and securely engaged therewith. The projecting portion of the pin provides a head upon which the tooth form may be cast. Preferably the body member is generally frustoconical in configuration with a planar surface and diametrically opposed rib both extending the length thereof; the pin extends beyond the narrow end and has a notch adjacent its point of exit.

9 Claims, 9 Drawing Figures

COMPOSITE DOWEL PIN FOR DENTAL MODELS

BACKGROUND OF THE INVENTION

Dowel pins on which tooth forms are cast for use in dental models are well known, two of such pins being described or claimed in U.S. Pat. No. 3,277,576 granted on Oct. 11, 1966 to Donald E. Kraft and U.S. Pat. No. 3,521,354 granted on July 21, 1970 to Alfred J. Stern and Harold L. Stern.

Generally, however, the dowel pins heretofor developed have been of machined metal, thus being relatively expensive, or integrally molded of synthetic resin and thus sacrificing some rigidity for economy. The dowel pins also generally have one or more planar surfaces extending the lengths thereof to index the pin upon insertion into the model base and to prevent rotation within the base, this often proving inadequate in preventing rotation especially if the dowel pin is not fully inserted into the base.

In Stern U.S. Pat. No. 3,521,354 a composite metal/plastic structure is described wherein the dowel pin is plastic and comprises a longitudinally tapered body having a shank extending from its wide end with a metal pin inserted in and extending longitudinally from the shank. The pin does not extend through the body and is present to enable mounting the dowel pin directly in the mold and does not enhance structural rigidity.

Accordingly, it is an object of the present invention to provide a novel composite dowel pin that is readily and economically fabricated and which is rugged and simple to use.

It is also an object to provide such a dowel pin having substantial structural rigidity and which permits relatively rapid fabrication of the tooth forms.

Another object is to provide such a dowel pin having a cross sectional configuration that provides improved resistance to rotation upon insertion into the model base.

SUMMARY OF THE INVENTION

It has now been found that the foregoing and related objects of the present invention may be readily attained in a composite dowel pin for dental models comprising a metal pin and an elongated body member of synthetic resin. The pin extends longitudinally through the body member and projects beyond at least one end thereof, and has an external configuration providing interlocking engagement with the body member to prevent relative movement therebetween. The body member tapers longitudinally from the end beyond which the pin projects to a reduced dimension at the other end thereof, the projecting portion of the pin providing a head upon which may be cast a tooth form. The body member has a non-circular cross sectional configuration to index the dowel pin upon insertion into a model base and thereafter prevent rotation within the model base.

In the preferred embodiment the pin has a portion projecting beyond the other end of the body member to provide a shank which has a notch therein adjacent its juncture with the other end of the body member. The non-circular cross sectional configuration of the body member includes a planar portion and a rib having an arcuate cross section extending along the length thereof to provide a locating flat and projection, the rib being spaced about the periphery of the body member from the flat.

Also in its preferred aspect the head includes a portion having a circular cross section adjacent the body member and a portion having a rectangular cross section spaced therefrom with a width greater than and a thickness less than the diameter of that portion having the circular cross section. The external configuration of the pin includes a portion having a polygonal cross section which provides the interlocking engagement with the body member.

DETAILED DESCRIPTION OF THE ILLUSTRATED EMBODIMENT

Figure 1:
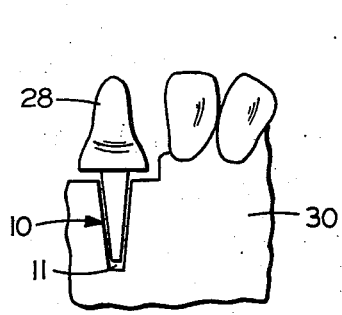
FIG. 1 is a fragmentary elevational view of a tooth model utilizing the composite dowel pin of the present invention inserted into a model base with a portion of the base broken away to show the dowel pin and with the bottom end portion of the dowel pin broken away.
Figure 3:
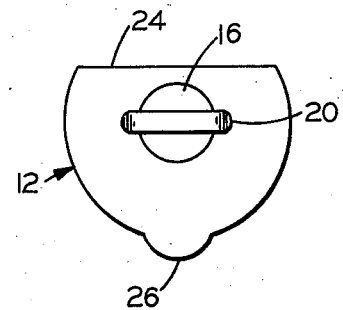
FIG. 3 is a plan view of the dowel pin of FIG. 2 drawn to a further enlarged scale.
Figure 4:
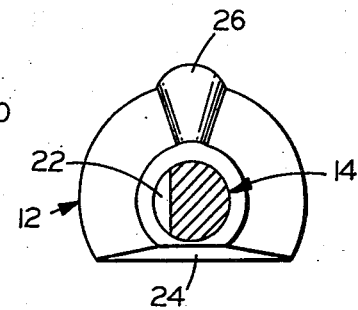
FIG. 4 is a cross sectional view along the line 4—4 of FIG. 2 drawn to an enlarged scale.

Turning first to FIG. 1 of the attached drawing, a composite dowel pin of the present invention is generally designated by the numeral 10 and is seated in a tapered recess 11 of the model base 30. A tooth form 28 is carried upon the exposed or upper end thereof.

Figure 2:
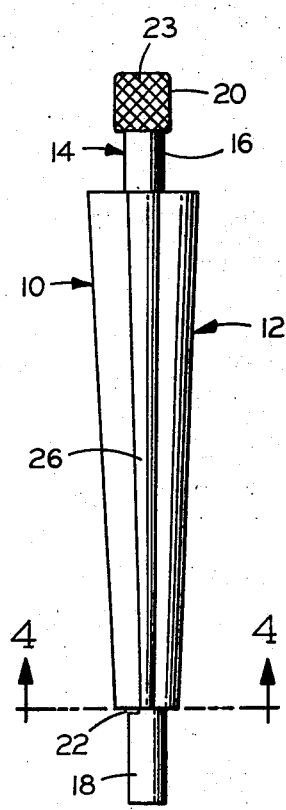
FIG. 2 is a front elevational view of the composite dowel pin of the present invention to an enlarged scale from that of FIG. 1.
Figure 5:
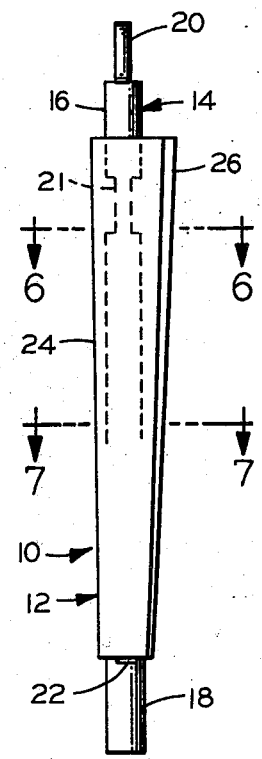
FIG. 5 is a side elevational view of the dowel pin with a portion of the pin shown in phantom line for clarity of illustration and on the scale of FIG. 2.

Turning now in detail to FIGS. 2 and 5, the composite dowel pin 10 comprises a body member generally designated by the numeral 12 and a pin generally designated by the numeral 14 extending longitudinally through and outwardly of both ends of the body member 12 to provide a head 16 and a shank 18. The body member 12 is formed of synthetic resin and the pin 14 of metal, the resultant composite structure having a structural rigidity greater than that of dowel pins formed integrally or completely from synthetic resin.

As best seen in FIGS. 2, 4, 6 and 7, the body member 12 tapers from one end to a reduced section at the other end with its cross sectional configuration deviating from circular due to the planar surface 24 and diametrically opposed rib 26 of arcuate cross section extending the length thereof. The planar surface 24 and rib 26 function to index the dowel pin 10 upon insertion into a cooperatively configured cavity 11 in a model base 30 and thereafter prevent rotation of the dowel pin 10 within the cavity 11. The rib 26 has been included in addition to the conventional planar surface 24 to augment the indexing and anti-rotational effect of the non-circular cross section. As seen the rib 26 tapers to a reduced width at the reduced end portion of the body member 12.

Figure 8:
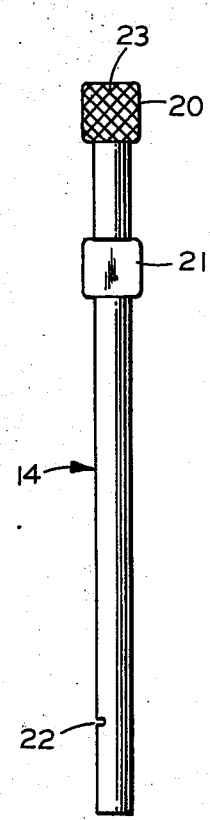
FIG. 8 is a front elevational view of the metal pin to the scale of FIG. 2.
Figure 9:
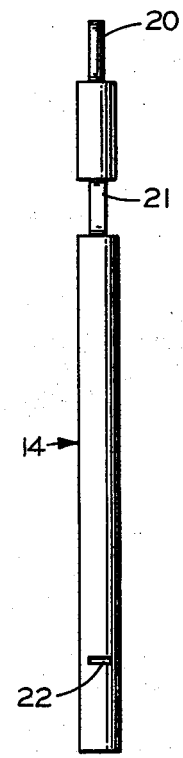
FIG. 9 is a side elevational view of the metal pin.
Figure 6:
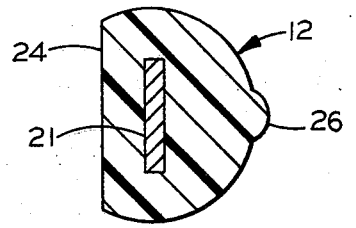
FIG. 6 is a cross sectional view along the line 6—6 of FIG. 5 and drawn to an enlarged scale.
Figure 7:
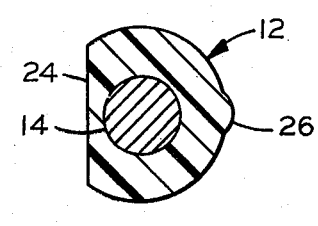
FIG. 7 is a cross sectional view along the line 7—7 of FIG. 5 and drawn to an enlarged scale.

The pin 14 is seen best in FIGS. 8 and 9 and has a circular cross section over most of its length as illustrated in FIG. 7 and two flat portions 20, 21 of rectangular cross section each having a width greater than and a thickness less than the diameter of the pin 14 as illustrated in FIGS. 6 and 9. The flat portion 21 provides interlocking engagement between the pin 14 and body member 12 to prevent relative movement therebetween. The flat portion 20 on the head 16 has knurls 23 on its major surfaces, the function of which will be described shortly. In the illustrated embodiment, the shank 18 has a notch 22 therein located adjacent its juncture with the body member 12 to facilitate breaking away this portion at a stage during fabrication, but this is not essential to use of the composite dowel pin.

In making the composite dowel pin of the present invention, the pin 14 is initially formed with the desired flat portions 20 and 21 and the notch 22 if so desired. The beneficial knurls 23 on the flat portion 20 are also formed in the surfaces thereof. Most conveniently, the resin of the body 12 is then injection molded thereabout with the flat portion 21 ensuring substantial elimination of any tendency towards relative movement.

Referring to FIGS. 1 and 2 to describe the manner in which the dowel pin 10 is used in making dental models, a tooth form 28 is cast onto the head 16 using conventional methods and apparatus (not shown). The reduced dimension in one direction of the flat portion 20 relative to the pin 14 initially provides a relatively large degree of freedom in positioning the head 16 within the space of the model die (not shown). Upon casting the tooth form 28 onto the head 16, the flat portion 20 and knurls 23 provide interlocking engagement between the tooth form 28 and head 16 to prevent the tooth form 28 from being disengaged therefrom or from relative rotation. The substantially cylindrical configuration of the shank 18 facilitates supporting and placing the dowel pin 10 during the casting process using a conventional machine (not shown), and reduces the potential for damage to the dental model during separation thereof from the die. The shank 18 may be removed from the dowel pin 10 after separation of the model from the die and prior to insertion into the model base 30, the notch 22 facilitating breaking the shank 18 from the pin 14 although it may be cut readily even in the absence of such a notch.

The pin is conveniently formed of rigid stainless steel wire with the flat portions thereof resulting from flattening of the wire in a suitable die which can also produce desired knurls. However, it may also be formed by casting or other suitable means and other relatively corrosion resistant metals may be employed such as brass, bronze, etc. In the preferred embodiment the head of the pin has a rectangular cross section through a portion of its length, but it may have any cross sectional configuration which prevents rotation of the cast tooth relative to the dowel pin. Similarly the flat portion interlocking with the body member may have a different configuration.

Normally the synthetic resin body member is molded onto the metal pin, but the pin may be inserted through a passage in the body member and any of the many means for fixedly mounting a core in a sleeve utilized, such as crimping, adhesive application, and solvent and heat sealing. An advantage resulting from molding synthetic resin to form the body member is that it makes a wider variety of cross sectional configurations economically feasible than if it were machined of metal. In this manner, it is simple to add the rib and obtain the resultant improvement in rotational resistance when the dowel pin is inserted into a base. The preferred cross sectional configuration of the body member is that illustrated, but the rib may be spaced anywhere about the arcuate sectional periphery. The body member may have other non-circular cross sectional configurations which provide indexing of the dowel pin upon insertion into a model base and thereafter prevent rotation.

The dowel pin preferably has a shank prior to casting the model to facilitate mounting and positioning as previously described, but it need not have one. The shank, if provided, may be retained subsequent to separation of the model from the die if the model base is configured to receive it.

Thus, it can be seen from the foregoing specification and drawing that the composite dowel pin of the present invention is readily and economically fabricated and is rugged and simple to use. The dowel pin has substantial structural rigidity and permits relatively rapid fabrication of the tooth forms. The dowel pin also has a cross sectional configuration that provides improved resistance to rotation upon insertion into a model base.

Having thus described the invention, We claim:

1. A composite dowel pin for dental models comprising a metal pin and an elongated body member of synthetic resin molded about said metal pin and having a bore extending longitudinally therethrough, said metal pin extending longitudinally through the length of said bore of said body member and projecting beyond at least one end thereof, said metal pin having an external configuration providing interlocking engagement with the wall of said body member defining said bore to prevent relative movement therebetween, said body member tapering longitudinally from said one end to a reduced dimension at the other end thereof, the portion of said metal pin projecting beyond said one end of said body member providing a head with at least a portion of non-circular cross section upon which may be cast a tooth form, and said body member having a non-circular cross sectional configuration to index said dowel pin upon insertion into a model base and thereafter prevent rotation within the model base.

2. The composite dowel metal pin of claim 1 wherein said pin has a portion projecting beyond said other end of said body member to provide a shank.

3. The composite dowel pin of claim 2 wherein said shank has a notch therein adjacent the juncture of said shank with said other end of said body member.

4. The composite dowel pin of claim 1 wherein said non-circular cross sectional configuration of said body member includes a planar portion extending along the length thereof to provide a locating flat.

5. The composite dowel pin of claim 4 wherein said non-circular cross sectional configuration of said body member further includes a rib having an arcuate cross section extending along the length thereof and spaced about the periphery thereof from said locating flat to provide a locating projection.

6. The composite dowel pin of claim 1 wherein said non-circular cross sectional configuration of said body member includes a rib extending along the length thereof to provide a locating projection.

7. The composite dowel pin of claim 1 wherein said head includes a second portion having a circular cross section adjacent said one end of said body member and wherein said non-circular portion has a polygonal cross section and is spaced therefrom.

8. The composite dowel pin of claim 7 wherein said head portion of polygonal cross section is of rectangular cross section and has a width greater than and a thickness less than the diameter of said head portion of circular cross section.

9. The composite dowel pin of claim 1 wherein said external configuration of said metal pin includes a portion having a polygonal cross section providing said interlocking engagement with said body member.

* * * * *